(12) United States Patent
Karg et al.

(10) Patent No.: US 8,043,865 B2
(45) Date of Patent: *Oct. 25, 2011

(54) METERING DOSES OF SAMPLE LIQUIDS

(75) Inventors: Jeffrey A. Karg, Hopkinton, MA (US);
Douglas W. Kroncke, Boston, MA (US)

(73) Assignee: Molecular BioProducts, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/873,625

(22) Filed: Sep. 1, 2010

(65) Prior Publication Data

US 2011/0027906 A1 Feb. 3, 2011

Related U.S. Application Data

(63) Continuation of application No. 12/563,439, filed on Sep. 21, 2009, which is a continuation of application No. 10/911,845, filed on Aug. 5, 2004, now Pat. No. 7,592,185.

(60) Provisional application No. 60/544,897, filed on Feb. 17, 2004, provisional application No. 60/547,958, filed on Feb. 27, 2004.

(51) Int. Cl.
*G01N 1/10* (2006.01)
(52) U.S. Cl. ........ 436/180; 422/501; 422/514; 422/524; 73/863.32; 73/864; 73/864.01
(58) Field of Classification Search .................. 422/501, 422/514, 524, 931; 73/863.32, 864, 864.01, 73/863.73; 436/180
See application file for complete search history.

(56) References Cited

U.S. PATENT DOCUMENTS

| 262,126 | A | 8/1882 | Root |
| 392,999 | A | 1/1888 | Esson et al. |
| 2,046,873 | A | 7/1936 | Garrison |
| 2,260,888 | A | 10/1941 | Davis |
| 2,427,606 | A | 9/1947 | Johnson |
| 2,667,075 | A | 1/1954 | Blum et al. |

(Continued)

FOREIGN PATENT DOCUMENTS

DE 3115568 4/1982

(Continued)

OTHER PUBLICATIONS

Pessenda, Garcia, P. "European Search Report", European Patent Office, Appl. No. 11003860.1—1270, mailed on Jul. 12, 2011 (7 pages).

*Primary Examiner* — Brian R Gordon
(74) *Attorney, Agent, or Firm* — Fish & Richardson P.C.

(57) ABSTRACT

A device and method of metering and mixing a dose of a sample liquid with a diluent liquid includes introducing a sample liquid into a channel defined in a housing. The housing defines a pocket open to the channel and sized to both collect a metered dose of the sample liquid, and to retain the collected dose by capillary force when the channel is emptied. The sample liquid is then removed from the channel under conditions that enable retention of the collected, metered dose of the sample liquid in the pocket. Following a cleaning step, a volume of diluent liquid is introduced into the channel to induce diffusion and mixing of the diluent liquid with the dose of sample liquid to form a mixture.

19 Claims, 20 Drawing Sheets

U.S. PATENT DOCUMENTS

| | | |
|---|---|---|
| 2,902,155 A | 9/1959 | Lundeen |
| 3,365,064 A | 1/1968 | Horan, Jr. |
| 3,649,218 A | 3/1972 | Pontigny |
| 3,834,241 A | 9/1974 | Garren et al. |
| 4,010,648 A | 3/1977 | Harris, Sr. et al. |
| 4,117,728 A | 10/1978 | Johnson |
| 4,212,204 A | 7/1980 | St. Amand |
| 4,408,968 A | 10/1983 | Inagaki et al. |
| 4,451,220 A | 5/1984 | Ito et al. |
| 4,454,760 A | 6/1984 | Carlisle |
| 4,563,104 A | 1/1986 | Saint-Amand |
| 4,564,451 A | 1/1986 | Cohen |
| 4,749,658 A * | 6/1988 | Jaekel et al. ............... 436/180 |
| 4,844,868 A | 7/1989 | Rokugawa |
| 4,877,585 A | 10/1989 | Perlman |
| 4,896,270 A | 1/1990 | Kalmakis et al. |
| 4,933,291 A | 6/1990 | Daiss |
| 5,084,241 A | 1/1992 | Parker |
| 5,226,462 A | 7/1993 | Carl |
| 5,260,030 A | 11/1993 | DeVaughn |
| 5,558,509 A | 9/1996 | Jirnov et al. |
| 5,620,662 A | 4/1997 | Perlman |
| 5,674,173 A * | 10/1997 | Hlavinka et al. ............... 494/17 |
| 5,722,926 A * | 3/1998 | Hlavinka et al. ............... 494/37 |
| 5,741,554 A | 4/1998 | Tisone |
| 5,770,151 A | 6/1998 | Roach et al. |
| 5,773,305 A | 6/1998 | Zabetakis et al. |
| 5,780,305 A | 7/1998 | Chisum |
| 5,851,491 A | 12/1998 | Moulton |
| 5,874,045 A | 2/1999 | Chisum |
| 5,906,570 A * | 5/1999 | Langley et al. ............... 494/45 |
| 5,906,751 A | 5/1999 | Parker |
| 5,961,927 A | 10/1999 | Isaacs et al. |
| 6,048,457 A | 4/2000 | Kopaciewicz et al. |
| 6,054,325 A | 4/2000 | Kedar et al. |
| 6,130,098 A | 10/2000 | Handique et al. |
| 6,165,417 A | 12/2000 | Swierkowski |
| 6,197,259 B1 | 3/2001 | Kelly et al. |
| 6,451,188 B1 | 9/2002 | Sundberg et al. |
| 6,482,362 B1 | 11/2002 | Smith |
| 6,706,538 B1 | 3/2004 | Karg et al. |
| 7,081,228 B1 | 7/2006 | Ito |
| 7,160,511 B2 * | 1/2007 | Takahashi et al. ............ 422/504 |
| 7,229,594 B2 | 6/2007 | Renaud et al. |
| 7,850,917 B2 * | 12/2010 | Ding et al. ...................... 422/81 |
| 2002/0187560 A1 | 12/2002 | Pezzuto et al. |
| 2003/0194353 A1 * | 10/2003 | Gilbert et al. ................. 422/100 |
| 2003/0198576 A1 | 10/2003 | Coyne et al. |
| 2003/0210607 A1 | 11/2003 | Gilbert et al. |
| 2004/0028566 A1 | 2/2004 | Ko et al. |
| 2004/0072367 A1 | 4/2004 | Ding et al. |
| 2004/0156746 A1 | 8/2004 | Larsen |
| 2004/0231438 A1 | 11/2004 | Schwartz |
| 2005/0095723 A1 | 5/2005 | DiTrolio et al. |

FOREIGN PATENT DOCUMENTS

| | | |
|---|---|---|
| EP | 0971235 | 1/2000 |
| EP | 1 304 167 | 4/2003 |
| WO | WO 9008075 | 7/1990 |
| WO | WO 9804358 | 2/1998 |
| WO | WO 9915876 | 4/1999 |
| WO | WO 9961881 | 12/1999 |
| WO | WO 0024511 | 5/2000 |
| WO | WO 0164345 | 9/2001 |
| WO | WO 03016832 | 2/2003 |

\* cited by examiner

METERING DOSES OF SAMPLE LIQUIDS

CROSS-REFERENCE TO RELATED APPLICATIONS

This application is a continuation (and claims the benefit of priority under 35 U.S.C. 120) of U.S. patent application Ser. No. 12/563,439, filed Sep. 21, 2009, which is a continuation of U.S. patent application Ser. No. 10/911,845, filed Aug. 5, 2004, which has issued as U.S. Pat. No. 7,592,185. U.S. patent application Ser. No. 10/911,845 claims the benefit of prior U.S. Provisional Application Ser. Nos. 60/544,897, filed Feb. 17, 2004, and 60/547,958, filed Feb. 27, 2004. The disclosure of the prior applications are considered part of (and are incorporated by reference in their entirety in) the disclosure of this application.

TECHNICAL FIELD

This invention relates to metering and mixing doses of a sample liquid with a diluent liquid within a liquid transfer device, such as with a pipette.

BACKGROUND

The science and economics of drug discovery has changed with developments in the areas of genomics, combinatorial chemistry and high-throughput screening. The number of targets has increased as a result of genomics while the number of small molecule compounds (samples) has dramatically increased as a result of combinatorial chemistry. This increase in targets and compounds has an exponential effect on the number of tests that need to be performed to increase the likelihood of finding a new chemical entity using high-throughput screening. Microliter amounts of target and sample must suffice for many screening assays, putting pressure on the automation industry to provide new tools to increase throughput, efficiency, and reduce R&D costs. Conventional R&D screening efforts use multiple variations of pipetting to move aliquots of the concentrated liquid sample from storage receptacles, to working receptacles, to dilution receptacles and finally to assay receptacles. This "reformatting" process, or "sample prep." adds complexity to the overall process, wastes valuable sample or target, and increases time and assay cost.

Disposable pipette tips and non-disposable, cleanable pipetting devices are commonly used for proportioning liquids. Pipette tips and pipetting devices include an input aperture at one end and a placement aperture at the other end for attachment to the pipetting device. The pipetting device often encompasses a piston-cylinder positive displacement mechanism. The pipette tip attaches to the pipetting device through a variety of mechanical connection schemes. A column of air connects the piston-cylinder mechanism to the pipette tip through a fluidic interface. Liquid is aspirated into the pipette tip when the pipette tip's input aperture is submerged in liquid while the piston-cylinder mechanism draws in. The air column and aspirated liquid draw into the pipette tip via a proportioned amount. The liquid is dispensed from the tip by reversing the direction of the piston-cylinder mechanism. The amount of liquid that may be aspirated and dispensed is limited by a number of factors including but not limited to: pipette tip material, pipette tip surface finish, input aperture capillary forces, liquid surface energy, and piston-cylinder mechanism limitations.

Tubes, capillary channels, and plate surfaces make-up categories of devices that are used in many market applications that involve the transfer of fluids. In the drug discovery market, new developments in the area of "chip" based systems involve capillary channels to move fluids through a myriad of systemic processes. In the diagnostic market, tubes and pipetting devices are used to perform a number of liquid tests, all burdened by the limited amount of source liquid vs. the number of tests that are desired to be run against those source liquids.

SUMMARY

In general, in one aspect the invention provides a method for metering and mixing a dose of a sample liquid with a diluent liquid and includes introducing a sample liquid into a channel defined in a housing, the housing defining a pocket open to the channel and sized to collect a metered dose of the sample liquid, and to retain the collected dose by capillary force when the channel is emptied; removing the sample liquid from the channel under conditions that enable retention of the collected metered dose of the sample liquid in the pocket; and then introducing a volume of diluent liquid into the channel to induce diffusion and mixing of the diluent liquid to form a mixture.

Some embodiments include cleaning the channel following the removal of the sample liquid from the channel and prior to the introduction of diluent liquid into the channel. The cleaning step includes introducing a cleaning liquid into the channel below the pocket; and then removing the cleaning liquid from the channel to flush any residual sample liquid from surfaces of the channel below the pocket.

In some cases the housing includes a tube defining the channel. In these cases, the tube can have an open lower end through which the sample liquid is introduced by drawing the liquid into the tube. The channel can be narrow and/or the pocket can be disposed on a portion of the channel wider than the channel at the open end of the tube. The pocket can include an upwardly extending notch defined in an interior wall of the tube. The surface of the tube can define a lower extent of the pocket that is substantially perpendicular to a longitudinal axis of the tube. In some embodiments, the pocket can be elongated and parallel to a longitudinal axis of the tube.

In some cases, the housing includes a laminated plate that defines the liquid channel, the pocket and an input orifice in fluid contact with the channel. In these cases, the sample liquid can be introduced and removed from the channel pneumatically.

In some embodiments, the method further includes dispensing a metered volume of the mixture into a destination well. The mixture can be dispensed by pneumatically propelling the mixture from the housing. Also, the mixture can be propelled from the housing by pressurized gas.

In some cases, the volume of diluent liquid introduced into the channel is in the range of between about 1 nanoliter and 1 milliliter.

In some embodiments, the housing defines a plurality of said pockets spaced apart from one another.

Implementations may include one or more of the following features. For example, the pocket can be formed from a method selected from the group consisting of molding, machining, welding, and coating or other suitable means for producing a capillary retainment feature. The pocket can be formed of a material secured to a material forming an inner surface of the housing. The pocket can be defined in a protrusion extending into the channel.

In another aspect, the invention provides a method of metering and mixing a dose of a sample liquid with a diluent liquid and includes drawing a sample liquid into a pipette defining an internal cavity and having an interior wall defining a pocket sized to collect a metered dose of the sample liquid; followed by expelling the sample liquid from the pipette under conditions that enable retaining the collected, metered dose of the sample in the pocket by capillary force; and then drawing a volume of the diluent liquid into the pipette a sufficient distance to contact the retained dose of sample liquid, to induce diffusion and mixing of the diluent liquid with the dose of sample liquid.

Some embodiments include cleaning the pipette after expelling the sample liquid from the pipette and prior to drawing the diluent liquid into the pipette. The cleaning step includes drawing a cleaning liquid into the pipette below the pocket; and then expelling the cleaning liquid from the pipette to flush any residual sample liquid from surfaces of the interior wall below the pocket.

In some embodiments, the method further includes dispensing a metered volume of the mixture into a destination well. The mixture can be dispensed by pneumatically propelling the mixture from the pipette. In some cases, the pipette further defines a capillary hole between an outer surface of the pipette and the internal cavity. In these cases, the mixture can be propelled from the pipette by forcing a pressurized gas into the internal cavity through the capillary hole.

In some cases, the internal cavity is narrower at a lower open end of the pipette than in an upper section of the pipette. In these cases, the pocket can be disposed in a portion of the internal cavity wider than the internal cavity at the open end of the pipette.

In some embodiments, a surface of the pipette defining a lower extent of the pocket is substantially perpendicular to a longitudinal axis of the pipette.

In some cases, the pocket is elongated and parallel to a longitudinal axis of the pipette.

In some embodiments, the volume of diluent liquid introduced into the internal cavity is in the range of between about 1 nanoliter and about 500 microliters.

In some cases, the pipette can define a plurality of said pockets spaced apart from one another, either parallel to the axis of the pipette or radially.

Implementations may include one or more of the following features. For example, the pipette can be formed from a synthetic resin. The pocket can be formed from a method selected from the group consisting of molding, machining, welding and coating or other suitable means for producing a capillary retainment feature. Also, the pocket can be defined as a protrusion extending into the internal cavity.

In yet another aspect, the invention provides a method of metering and mixing a plurality of doses of a sample liquid with a diluent liquid and includes providing an array of pipettes, each pipette defining an internal cavity and having an interior wall defining a pocket sized to collect a metered dose of a sample liquid; drawing the sample liquid into the pipettes; then expelling the sample liquid from the pipettes under conditions that enable retaining the collected, metered doses of the sample in pocket by capillary force; and then drawing a diluent liquid into the pipettes a sufficient distance to contact the retained doses of sample liquid, to induce diffusion and mixing of the diluent liquid with doses of the sample liquid.

Some embodiments include cleaning the pipettes after expelling the sample liquid from the pipettes and prior to drawing the diluent liquid into the pipettes. The cleaning step includes drawing a cleaning liquid into the pipettes below the pockets; and then expelling the cleaning liquid from the pipettes to flush any residual sample liquid from surfaces of the interior wall below the pocket.

In some embodiments, the method includes dispensing from each pipette a metered volume of the mixture into a destination well. Dispensing the metered volume can include pneumatically propelling the mixture from the pipettes. Also, each pipette can define a capillary hole between an outer surface of the pipette and the internal cavity, and the mixture can be propelled from the pipette by forcing a pressurized gas into the internal cavity through the capillary hole.

In some embodiments, the internal cavity is narrower at a lower open end of the pipette than in an upper section of the pipette. In these embodiments, the pocket can be disposed in a portion of the internal cavity wider than the internal cavity at the open end of the pipette.

In some cases, the pocket includes an upwardly extending notch defined in an interior wall of the pipette.

In some embodiments, a surface of the pipette defining a lower extent of the pocket is substantially perpendicular to a longitudinal axis of the pipette.

In some cases, the pocket is elongated and parallel to a longitudinal axis of the pipette.

In some embodiments, the volume of diluent liquid introduced into the internal cavity is in the range of between about 1 nanoliter and about 500 microliters.

In some cases, the pipette defines a plurality of said pockets spaced apart form one another, either parallel to the axis of the pipette or radially.

In some embodiments, the method includes dispensing a metered volume of the mixture in an array of liquid-receiving units. In these embodiments, the array of pipettes can be aligned directly above the array of liquid receiving units. The array of liquid receiving units can include a multi-well container. The multi-well container can be selected from the group consisting of a 96-well microtiter plate, a 384-well microtiter plate, and a 1536-well microtiter plate.

Implementations may include one or more of the following features. For example, the method can include dispensing a metered volume of the mixture onto a slide. Also, the method can include dispensing a metered volume of the mixture onto an electronic assay reading device.

In one aspect the invention provides a pipette including an elongated body having an outer surface and defining an internal cavity open at a lower end of the body; the body defining an opening in an upper portion of the body, through which air can be drawn from the cavity to draw fluids into the cavity through the lower end of the body; wherein the body has an interior wall defining a pocket open to the internal cavity, the pocket sized to collect and retain a metered dose of a liquid drawn into the cavity as the cavity is otherwise evacuated.

In some embodiments of the device, multiple molded internal or external pockets are present to provide a variable amount of final dispensed liquid volume. In some embodiments of the device, the internal or external pockets may be created by means other than molding, such as machined pockets, welded pockets, coated pockets, etc. In some embodiments of the device, the pockets may be secondary parts (such as overmolded or insert molded parts) that are attached to the liquid carrying device.

In some cases, the body further defines a capillary hole extending from the outer surface to the internal cavity.

In some cases, the pocket is disposed in a portion of the internal cavity wider than the cavity at the open end of the body.

In some embodiments, the pocket includes an upwardly extending notch defined in the interior wall of the body.

In some cases, the surface of the pipette defining a lower extent of the pocket is substantially perpendicular to a longitudinal axis of the body.

Implementations may include one or more of the following features. For example, the body can be formed from a synthetic resin. The body can define a plurality of said pockets spaced apart from one another, either parallel to the axis of the pipette or radially. Also, the pocket can be defined in a protrusion extending into the internal cavity.

Implementations of any of the foregoing may include one or more of the following features. The pocket is preferably sized to collect a metered dose of sample liquid between about 1 nanoliter and about 10 microliters in volume. More preferably, the pocket can be sized to collect a metered dose of sample liquid between about 5 nanoliters and about 10 microliters in volume. The pocket dimensions preferably range from between about 0.001 and 0.04 inch (0.025 and 1.02 millimeters) wide and between about 0.001 and 0.100 inch (0.025 and 2.54 millimeters) deep, more preferably, between about 0.008 and 0.020 inch (0.204 and 0.51 millimeters) wide and between about 0.008 and 0.04 inch (0.204 and 1.02 millimeters) deep. The length of the pocket preferably ranges from between about 0.01 and 1 inch (0.25 and 25 millimeters) long. A defining subset of features includes very small pocket wall radii, preferably ranging from between about 0.0005 and about 0.005 inch (0.013 and 0.127 millimeters) and a textured surface finish ranging from 2 microns to 256 microns. The diluent liquid can be moved reciprocally across the pocket multiple times, to induce mixing with the dose of sample liquid.

The devices disclosed herein are designed to capture a repeatable volume of source liquid by use of surface tension, geometry, or chemical adhesion. These devices may include tubes, plates, wells or reservoirs, capillary channels, disposable and non-disposable pipette tips, instruments whose main function is to aspirate and dispense liquids, and instruments whose main function is to move liquids through capillary channels, tubes, and pipette tips or across plates. All devices in this invention are intended to include the concept of metering a fixed or variable amount of source liquid, captured in the above mentioned pocket, followed by the dilution and mixing by a second liquid. This mixture may either be dispensed in full or in part, stored in the tube, pipette tip or channel, or moved through capillary channels or plates to another location.

This device can be made from materials common to the LifeSciences or Medical Diagnostics industry. The most common material for a disposable pipette tip is polypropylene, which may be filled with pigments, carbon, or other utility or function enhancing additives. Disposable pipette tips may also be made from other common molded plastics such as polypropylene, polystyrene, polycarbonate or others. Non-disposable pipette tips are often made from various grades of stainless steel, glass or other metals or plastics, and are often coated with hydrophobic coatings such as Teflon™ or Parylene™.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 17A is an enlarged view of area 17A in FIG. 17.

Like reference symbols in the various drawings indicate like elements. All pipette tip designations are intended to include disposable, non-disposable and tube-based liquid transportation devices.

DETAILED DESCRIPTION

Figures 1, 1A:
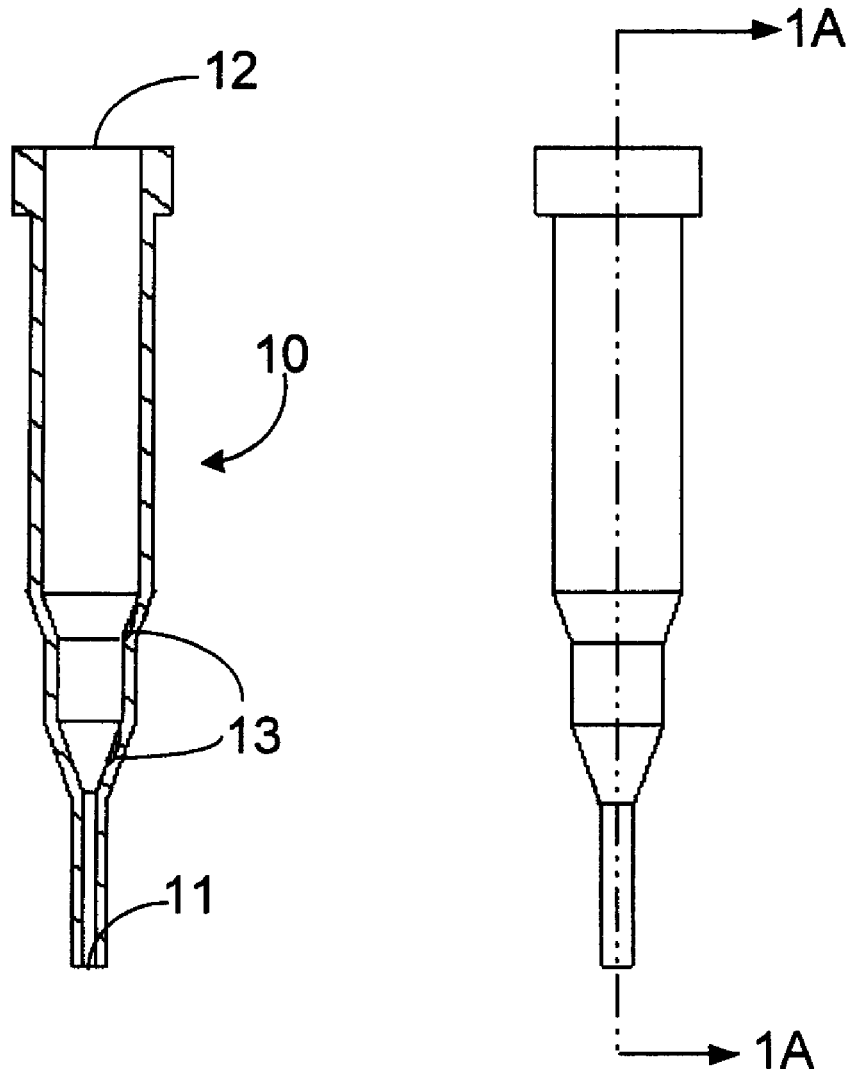
FIG. 1 is a side view of a pipette tip device.
FIG. 1A is a cross-sectional view, taken along line 1A-1A in FIG. 1.

FIGS. 1-1A show a first pipette tip device 10. Referring to FIG. 1A, the pipette tip 10 has an input aperture 11 and a placement aperture 12. The internal molded pockets 13 function to capture and hold a fixed amount of source liquid.

Figure 2:
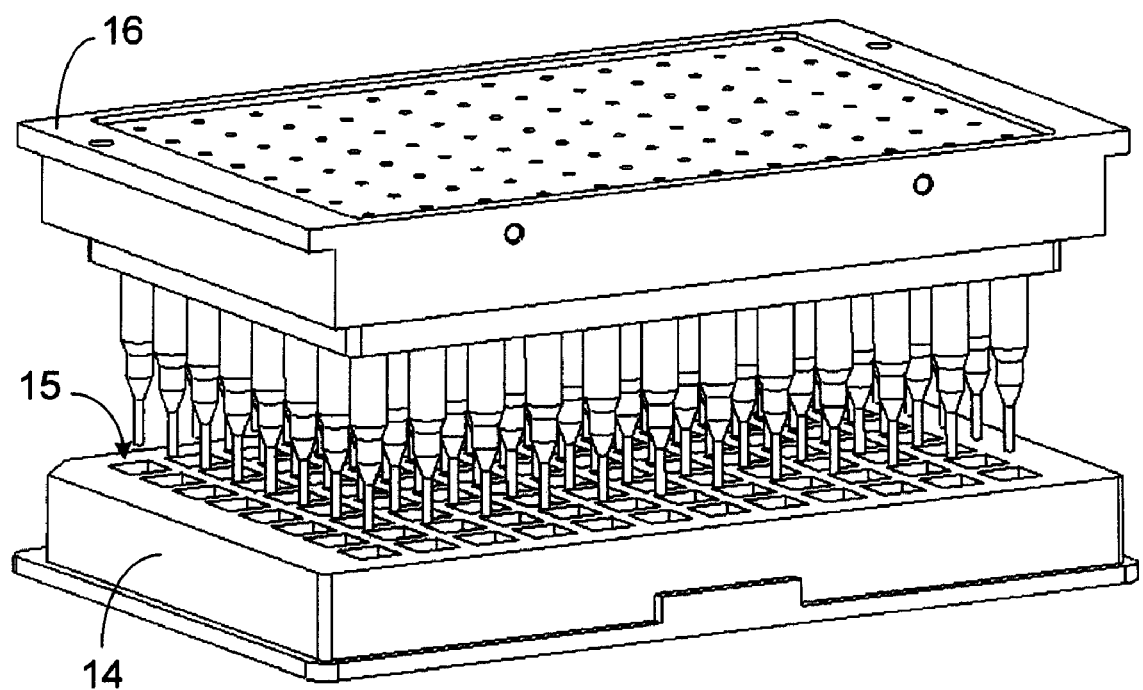
FIG. 2 is a perspective view of an array of pipette tips aligned over a receptacle plate.

FIG. 2 is a perspective view of an array of pipette tips 10 that are attached to a pipette adaptor array 16. The array of pipette tips 10 are aligned over a microtiter plate 14 which can include different array densities such as 96, 384, and 1536. Each pipette tip 10 is aligned with an individual well 15.

Figure 2A:
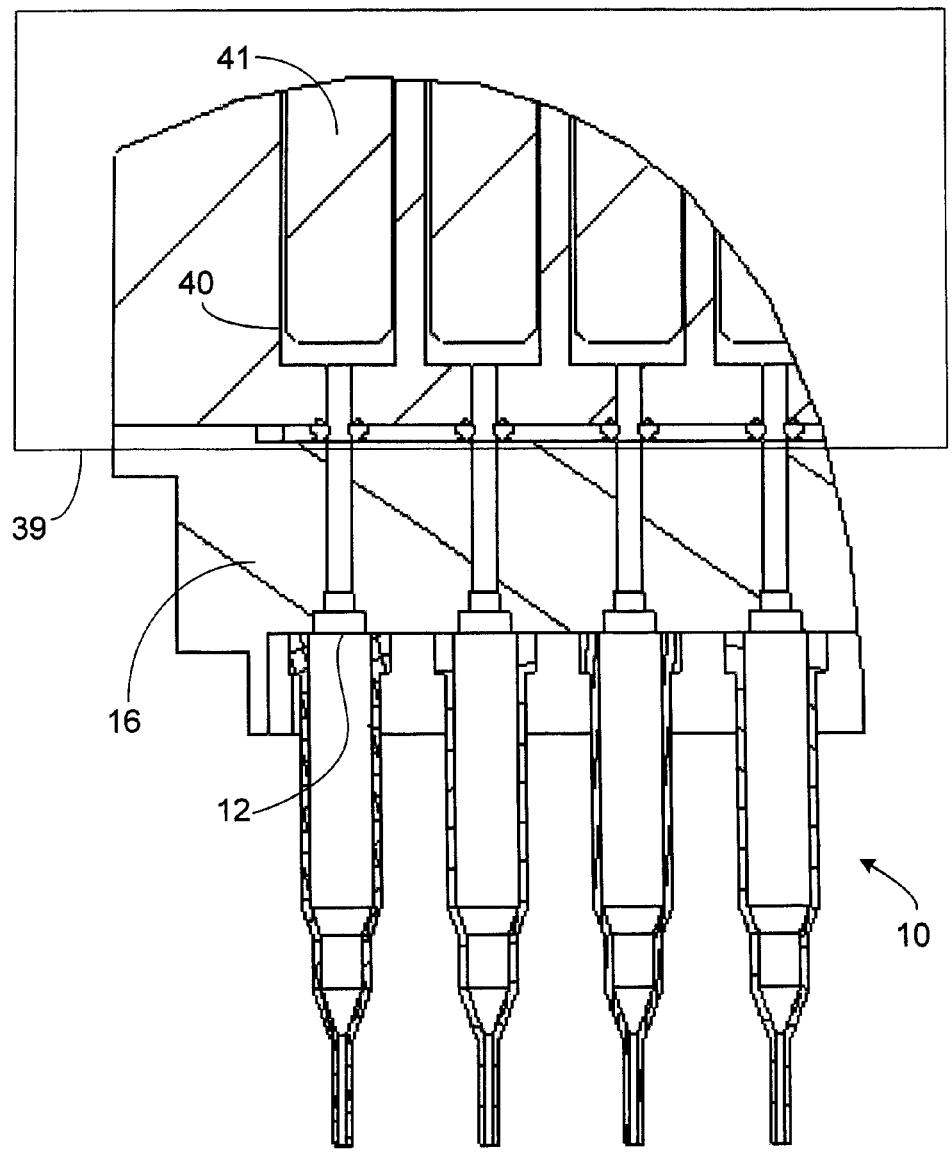
FIG. 2A is a sectional view of an array of pipette tips attached to a pipette adaptor array and a pipettor.

FIG. 2a is a sectional view of an array of pipette tips 10 that are attached to the pipette adaptor array 16 which attaches to the pipettor 39. The pipettor 39 is typically constructed of an array of pipettor cylinders 40 and pipettor pistons 41 used for positive displacement actuation.

In illustrating the operation of the pipette tip device 10, FIG. 3 through FIG. 10 are sequential.

Figure 3:
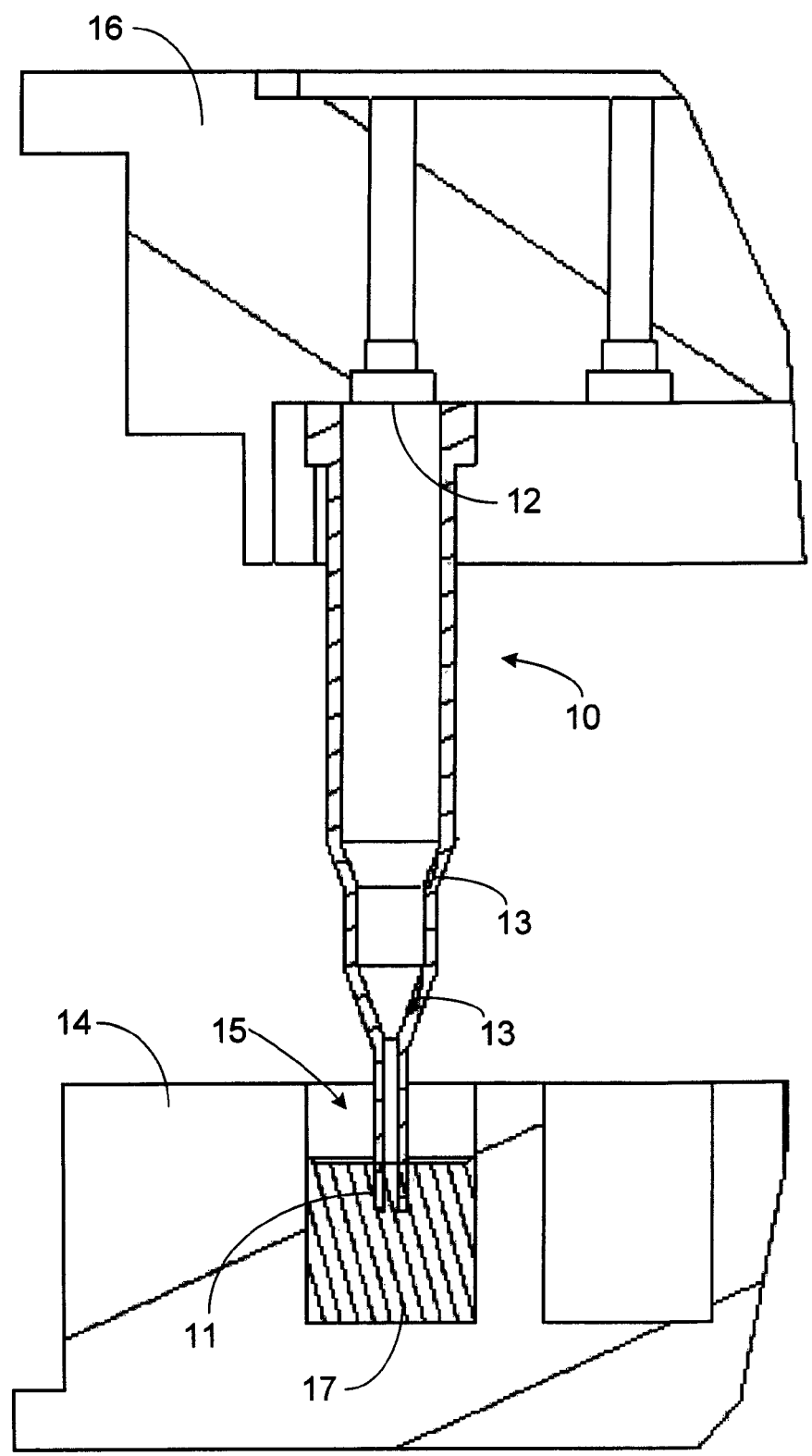
FIG. 3 is sectional view of a single pipette tip with the tip input aperture submerged in the source liquid stored in a source receptacle plate.

In FIG. 3, microtiter plate 14 includes source liquid 17 in each individual well 15. The pipette tip 10 input aperture 11 is submerged into the source liquid 17.

Figure 4:
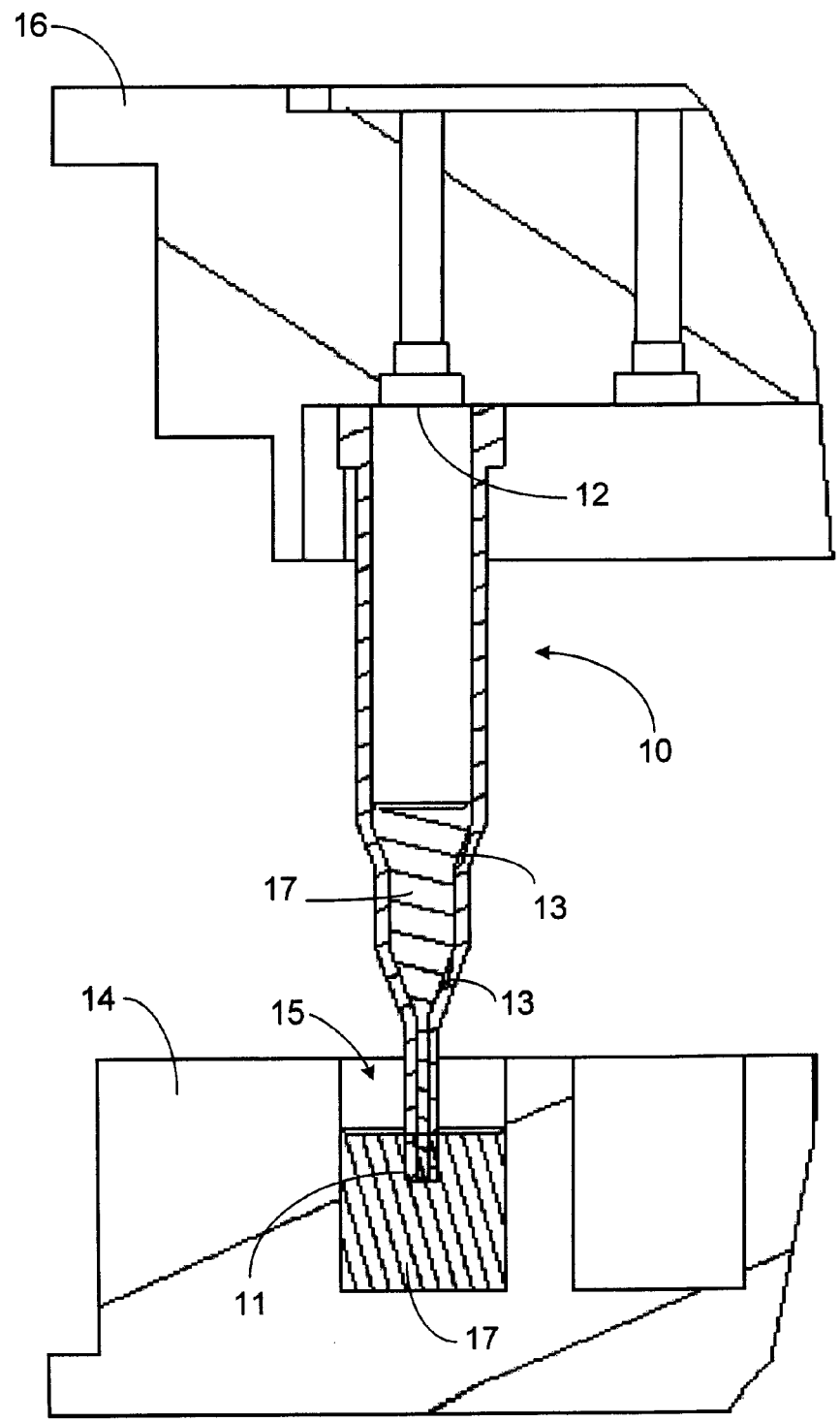
FIG. 4 is a sectional view of a single pipette tip with the source liquid aspirated into the input aperture and in contact with the internal molded pockets.

In FIG. 4, the pipettor 39, via the pipette adaptor array 16, aspirates source liquid 17 into pipette tip 10 through input aperture 11. The source liquid 17 is aspirated to the same level or higher than the internal molded pocket or pockets 13.

Figure 5:
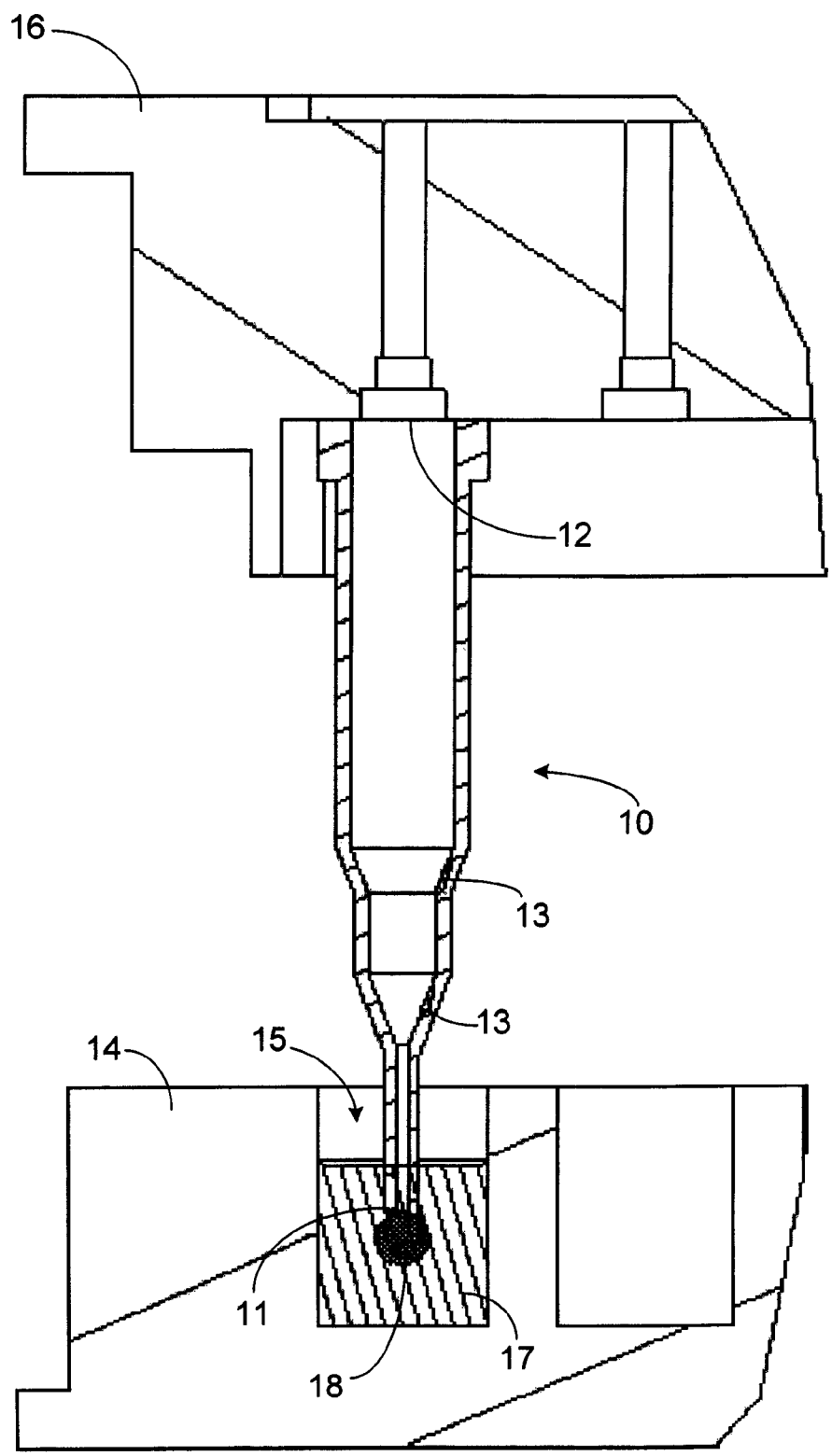
FIG. 5 is a sectional view of a single pipette tip with the source liquid dispensed back into the source receptacle plate.

In FIG. 5, the pipettor 39, via the pipette adaptor array 16, dispenses the source liquid 17 back out of pipette tip 10 through input aperture 11. Further motion of the pipette actuation device will begin to push air 18 out of the input aperture 11.

Figure 6:
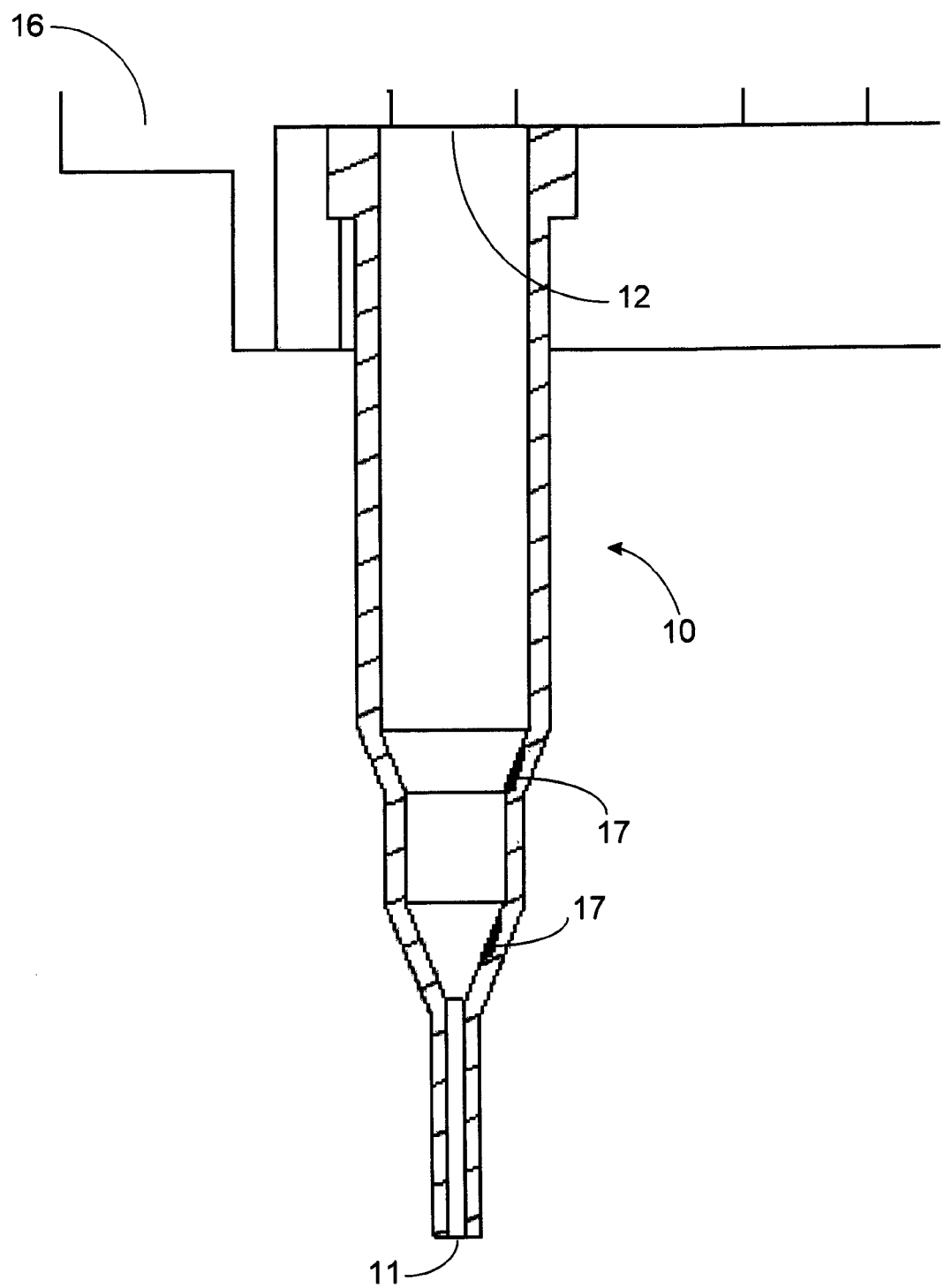
FIG. 6 is a sectional view of a single pipette tip showing the source liquid that remains inside the internal molded pipette tip pockets.

In FIG. 6, the microtiter plate 14 with the source liquid 17 is removed. The internal molded pockets have each captured and retained a fixed amount of source liquid 17.

Figure 6A:
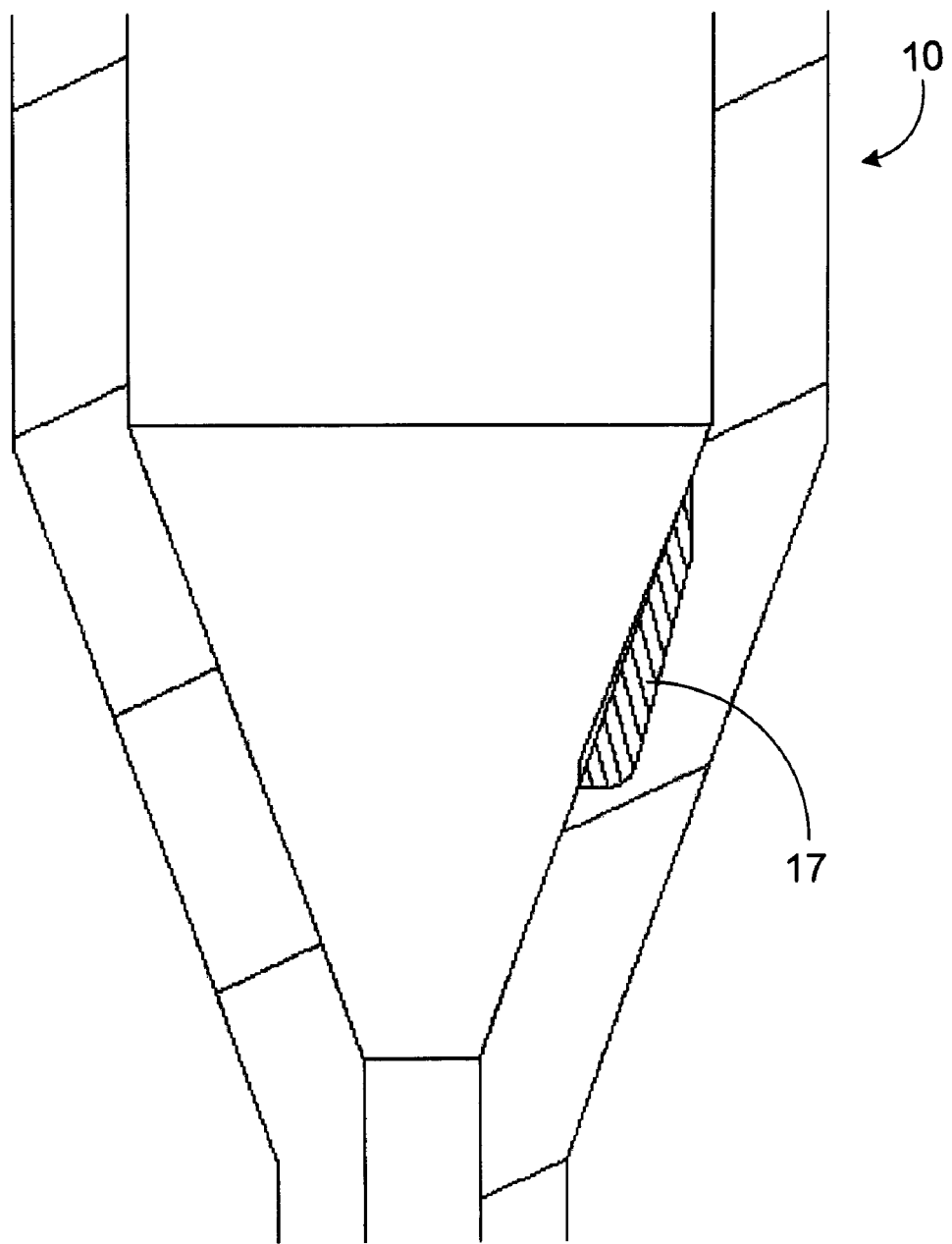
FIG. 6A is an enlarged sectional view of a single pipette tip showing the source liquid that remains inside one internal molded pocket.

In FIG. 6a, an enlarged view of the internal molded pocket 13 filled with source liquid 17 is presented.

Figure 7:
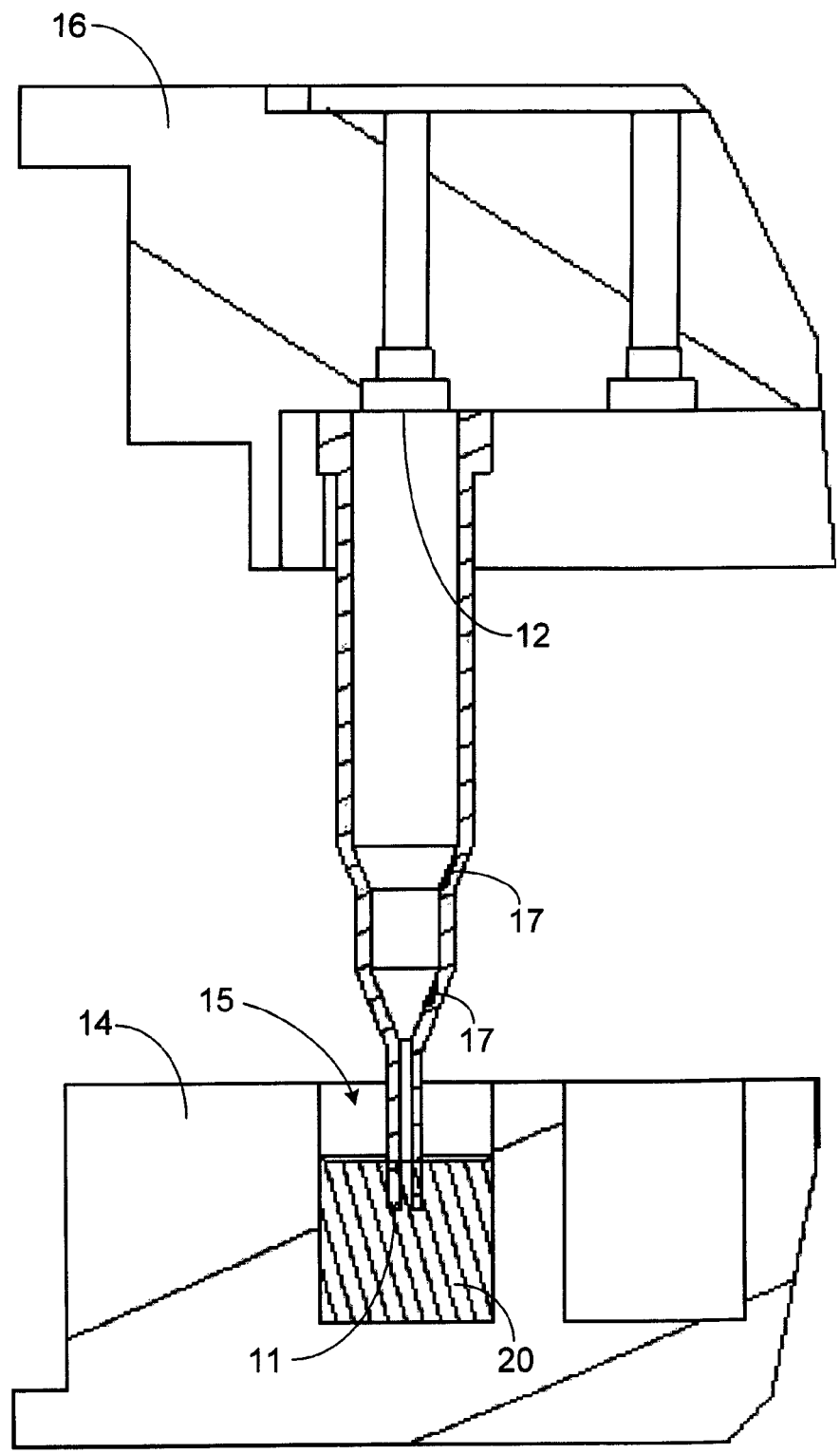
FIG. 7 is a sectional view of a single pipette tip with the pipette tip aligned over a system liquid receptacle device.

In FIG. 7, a second microtiter plate 14 with a diluting system liquid 20 in each individual well 15 is brought into contact with the pipette tip 10 such that the input aperture 11 is submerged.

Figure 8:
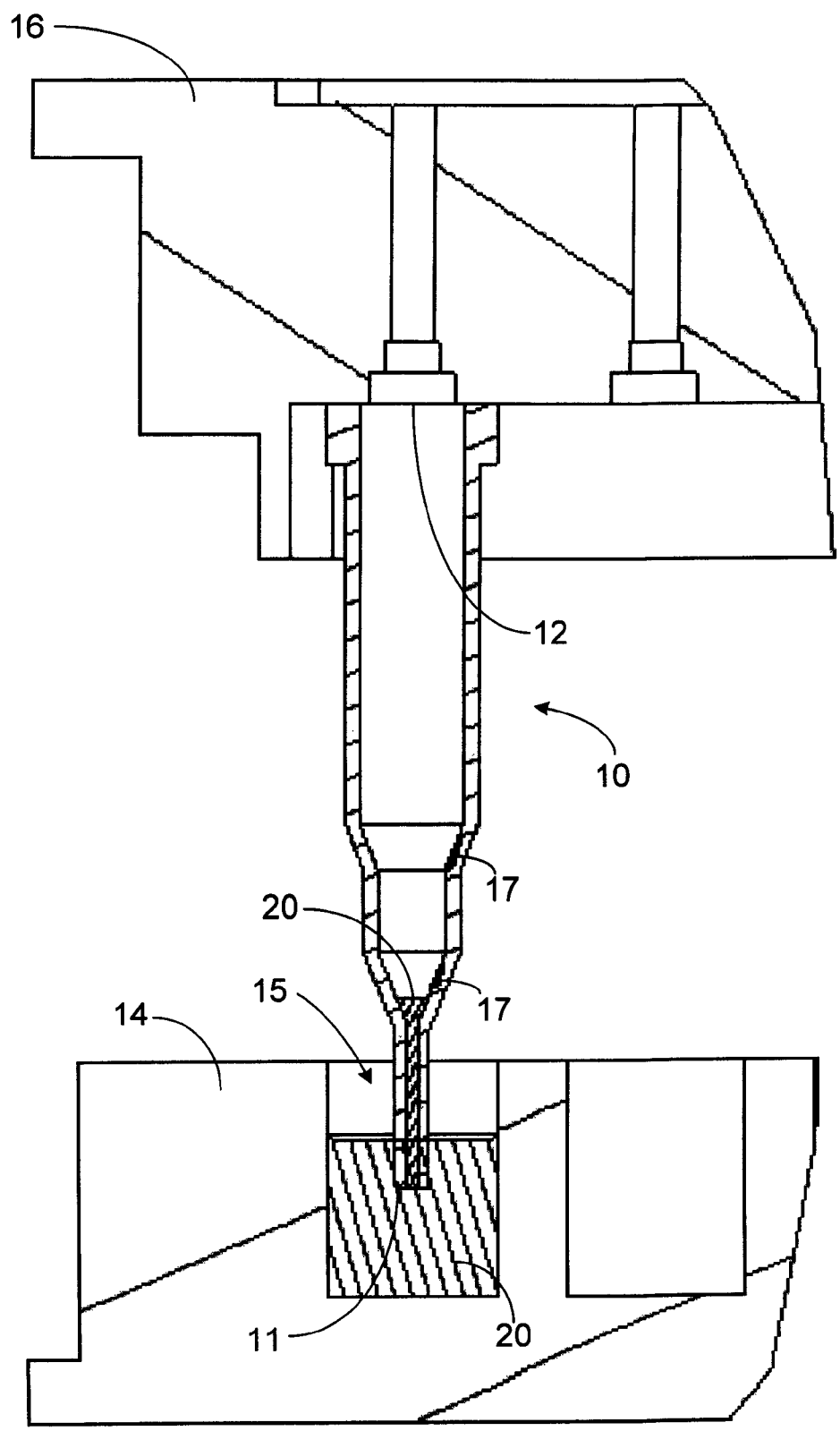
FIG. 8 is a sectional view of a single pipette tip with the system liquid aspirated into the input aperture.

In FIG. 8, the pipettor 39, via the pipette adaptor array 16, aspirates a fixed amount of diluting system liquid 20 into the pipette tip 10 through input aperture 11.

Figure 9:
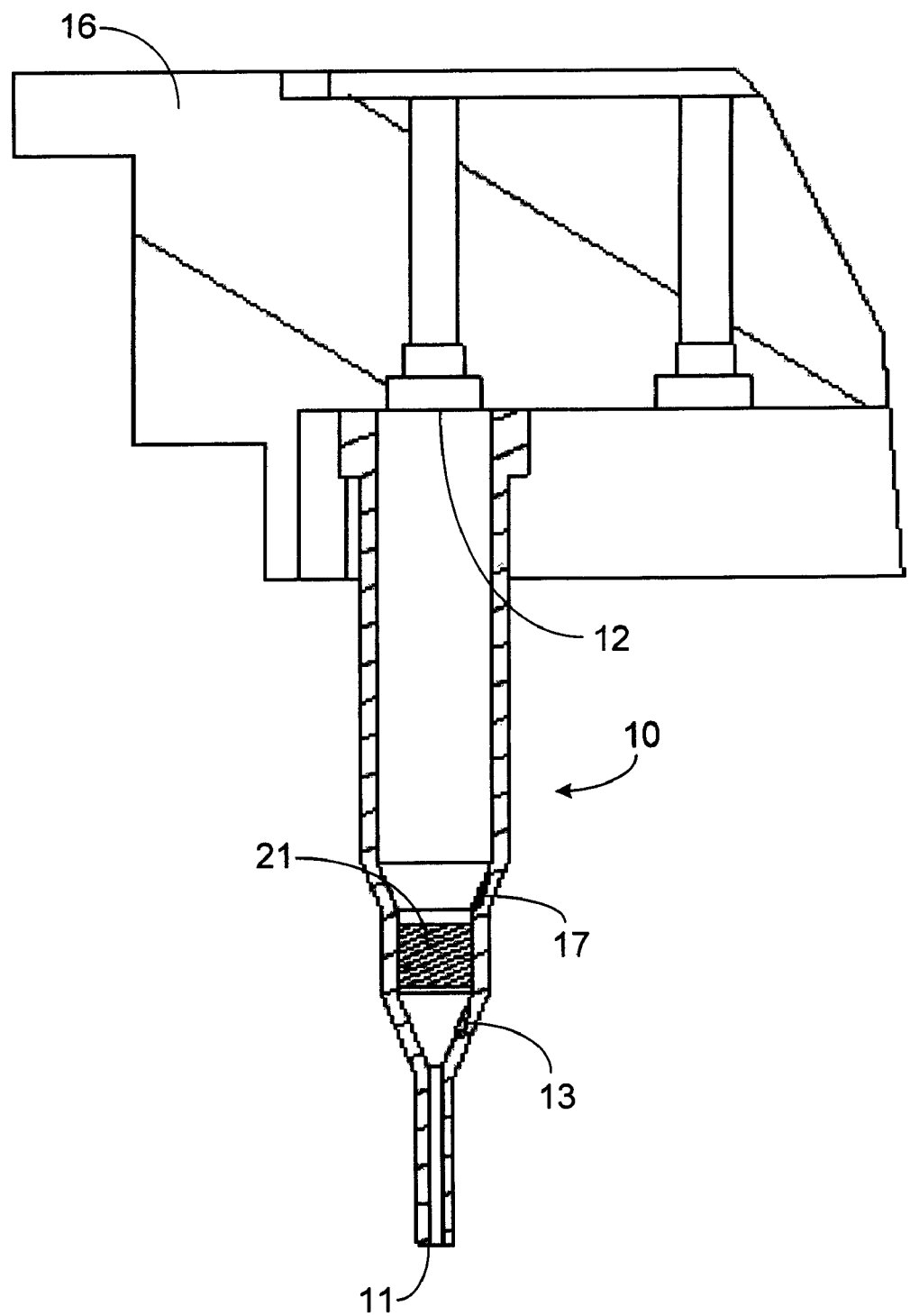
FIG. 9 is a sectional view of a single pipette tip with the aspirated system liquid located in between the lower and upper internal molded pocket.

In FIG. 9, the diluting system liquid microtiter plate 14 is removed. The pipettor 39, via the pipette adaptor array 16, aspirates the fixed volume of diluting system liquid 20 higher into the pipette tip 10. As the system liquid 20 passes by the internal molded pockets 13, the source liquid 17 that was retained in the pockets 13 is acquired by the diluting system liquid 20 to become mixture 21. The pipettor 39, via the pipette adaptor array 16, mixes the system liquid 20 up and down once or multiple times to create the mixture 21.

Figure 10:
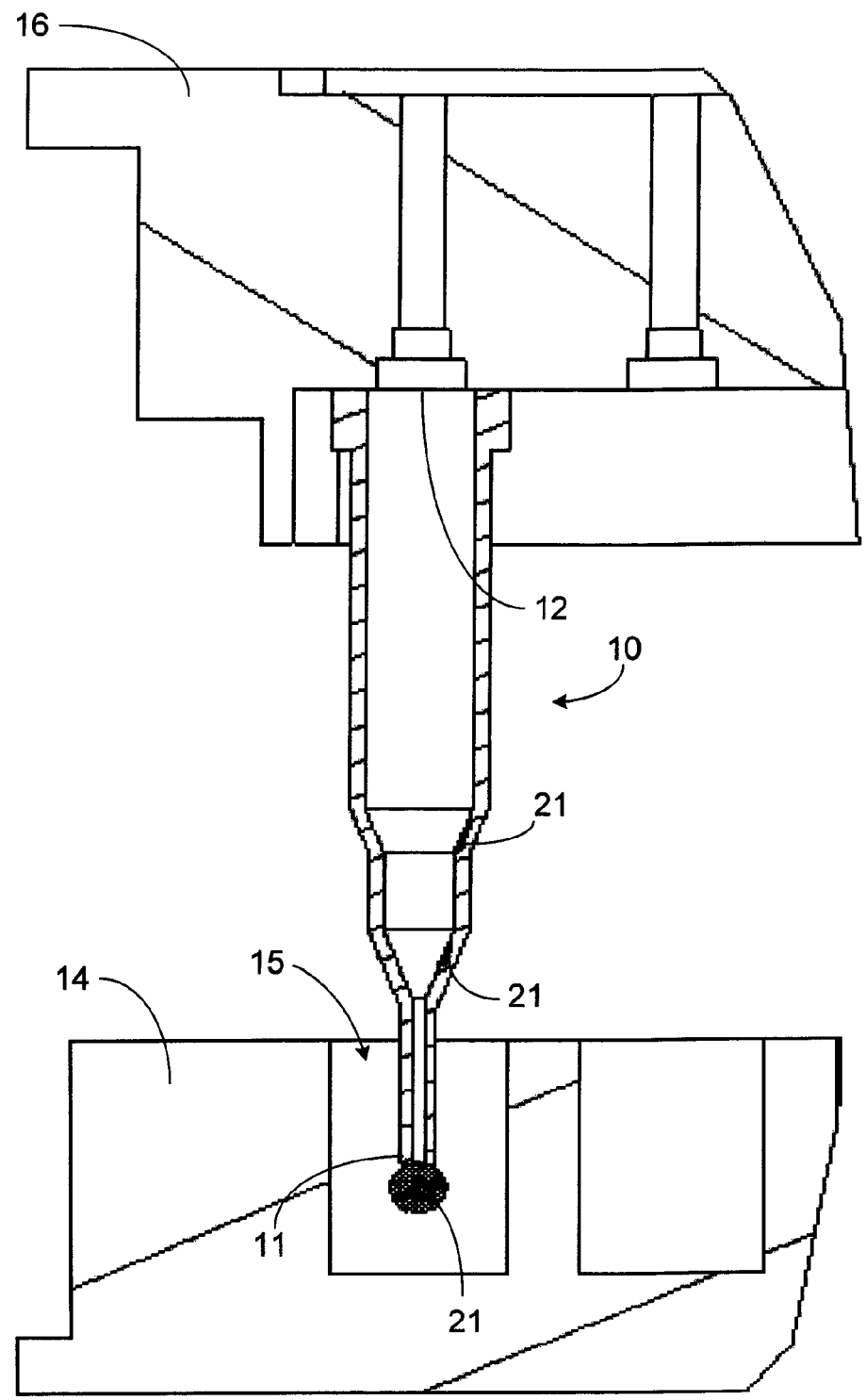
FIG. 10 is a sectional view of a single pipette tip showing the final destinations of the system liquid that has mixed with source liquid from the two internal molded pockets.

In FIG. 10, the pipettor 39, via the pipette adaptor array 16, dispenses the mixture 21 until all or a portion of the mixture becomes a droplet at the input aperture 11. The final step is to touch off the drop 21 to a solid wall of microtiter plate's 14 individual well 15. The mixture 21 droplet could also touch off into a liquid already present in the well 15.

Figures 11, 11A:
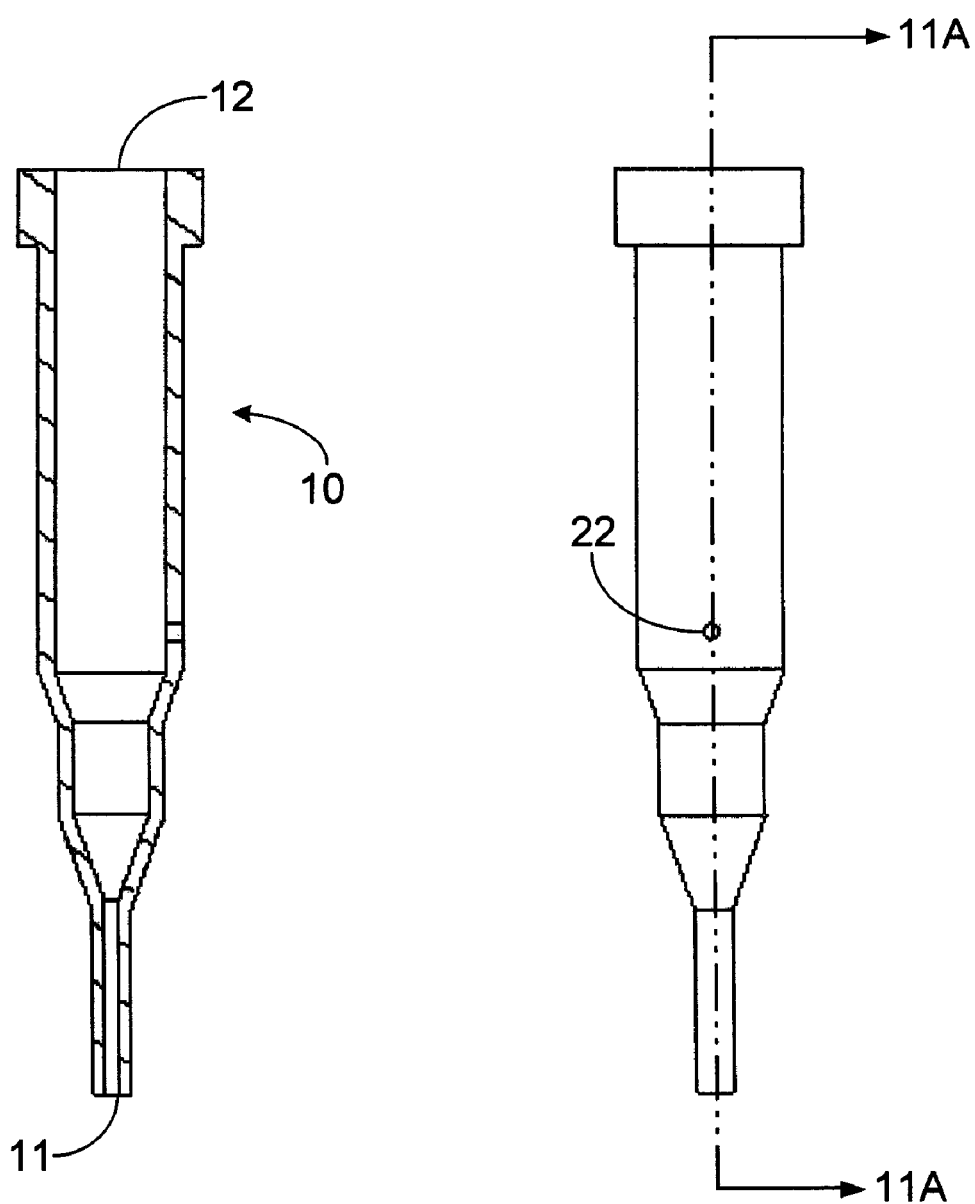
FIG. 11 is a side view of a single pipette tip showing a through-wall capillary hole.
FIG. 11A is a cross-sectional view, taken along line 11A-11A in FIG. 11.

Referring to FIGS. 11-11A, the pipette tip 10 can include a molded capillary hole 22 through one wall that can be used during a non-contact dispense routine. In this modification, an external instrument provides an air source that enters the capillary hole 22 and forces the mixture 21 out through the input aperture 11 into the microtiter plate 14. The molded capillary hole 22 could also be used to meter a specific volume of source liquid similar to a molded pocket.

Figures 12, 12A:
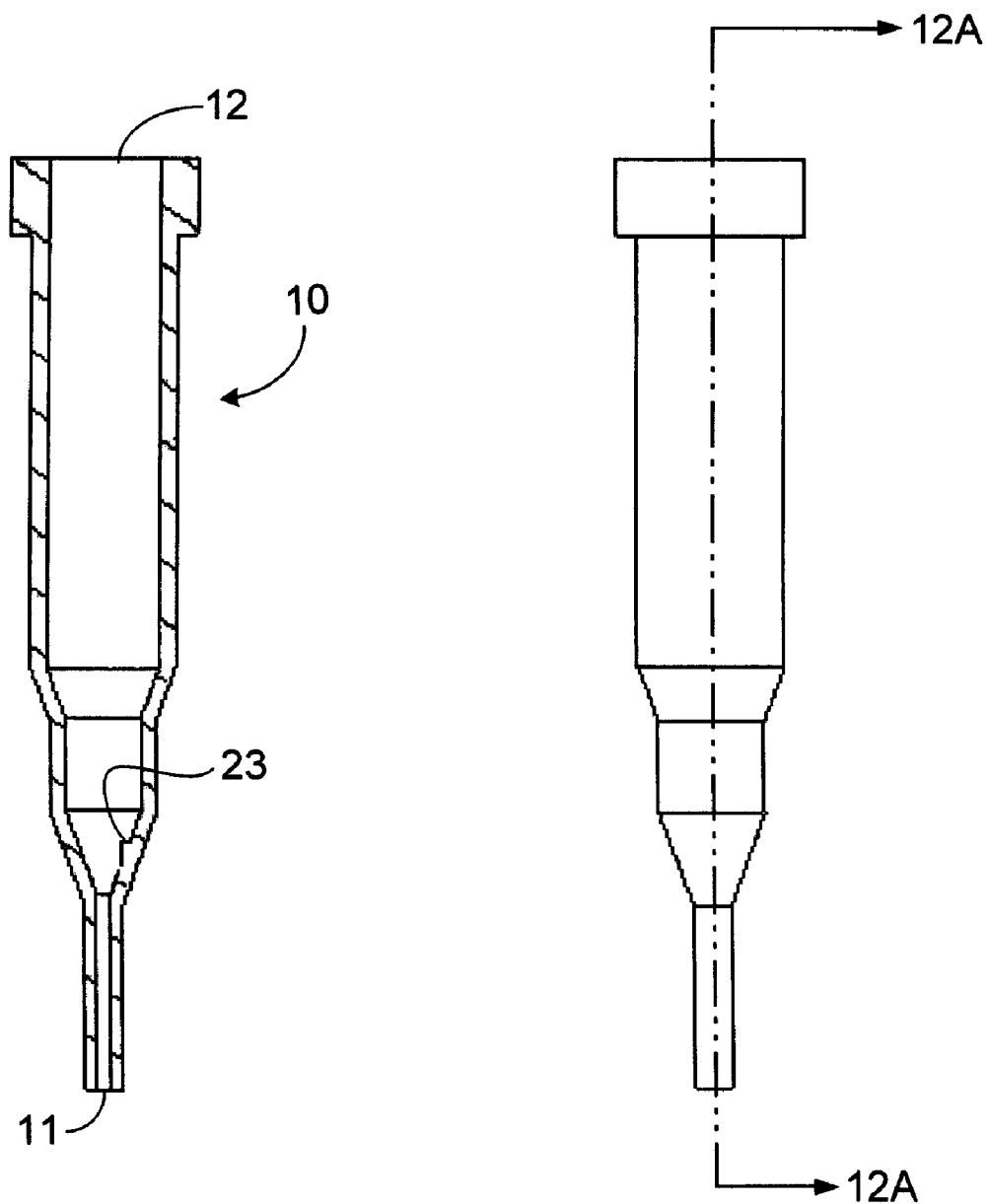
FIG. 12 is a side view of a single pipette tip.
FIG. 12A is a cross-section view, taken along line 12A-12A in FIG. 12, showing another internal molded element that extends from the inside surface into the pipette tip.

Referring to FIGS. 12-12A, the pipette tip 10 can include a protrusion with capillary like geometry or other modifications of the internal molded feature 23 for capturing and retaining the source liquid 17.

Figure 13:
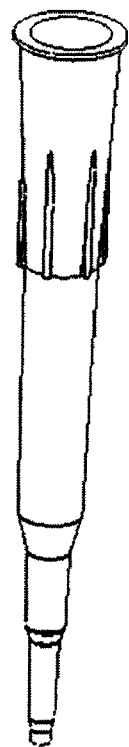
FIG. 13 is an isometric view of a single pipette tip.
Figure 13A:
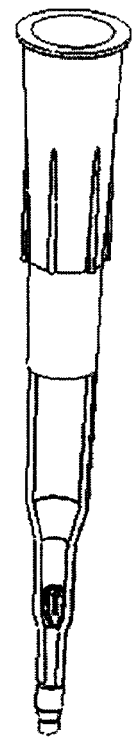
FIG. 13A is a cross-sectional view of the pipette tip illustrated in FIG. 13, showing another internal molded element that includes the metering geometry and surface finishes and that extends from the inside surface into the pipette tip.
Figure 13B:
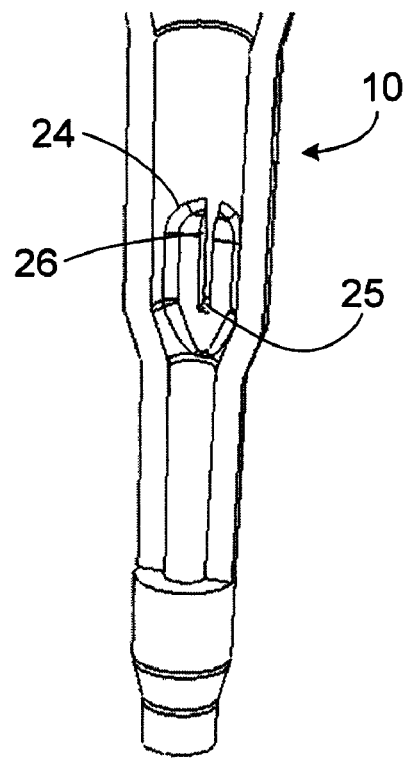
FIG. 13B is an enlarged detail of the cross-sectional view of the pipette tip shown in FIG. 13A.

Referring to FIGS. 13-13A, the pipette tip 10 includes a feature 24 that protrudes towards the center of the tip. The feature 24 can include very soft edges 25 so as to not trap any liquid in small geometric spaces. The feature includes the metering pocket 26 (or pockets) that capture the source liquid (not shown).

Figure 14:
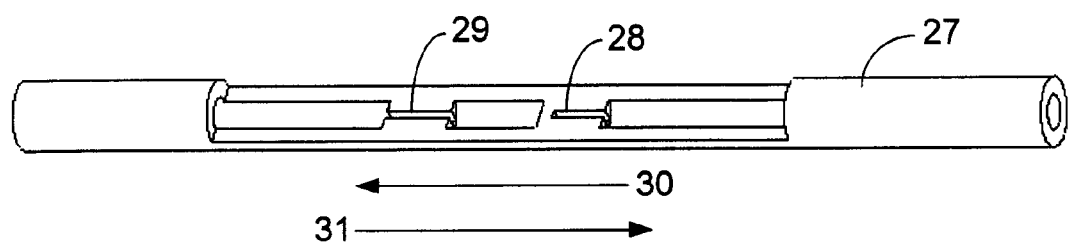
FIG. 14 is an isometric sectional view of a tube that contains one or more internal elements that function to meter the source liquid via geometry and surface finish.
Figure 14A:
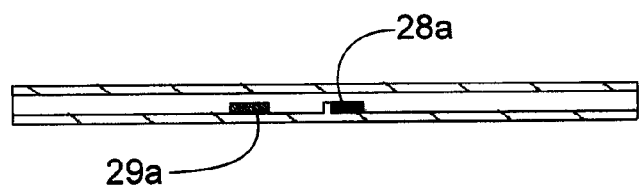
FIG. 14A is a cross-sectional side view of the tube illustrated in FIG. 14.

Referring to FIGS. 14-14A, a tube 27 is shown to include multiple pockets. For a clear visual in the drawing, the tube 27 is cut along its centerline to expose the internal pocket 28 and 29. The closed slot pocket 28 captures and retains source liquid 28a in the same manner as open slot pocket 29 captures and retains source liquid 29a. The source liquid could flow in the direction of arrow 30, and return in the opposite direction of arrow 31, leaving a precise amount of source liquid 28a and 29a in both pocket 28 and pocket 29 respectively. In some embodiments, the source liquid may be a finite slug and flow only in direction of arrow 30, leaving behind a precise amount of source liquid 28a and 29a in both pocket 28 and pocket 29 respectively.

Figure 15:
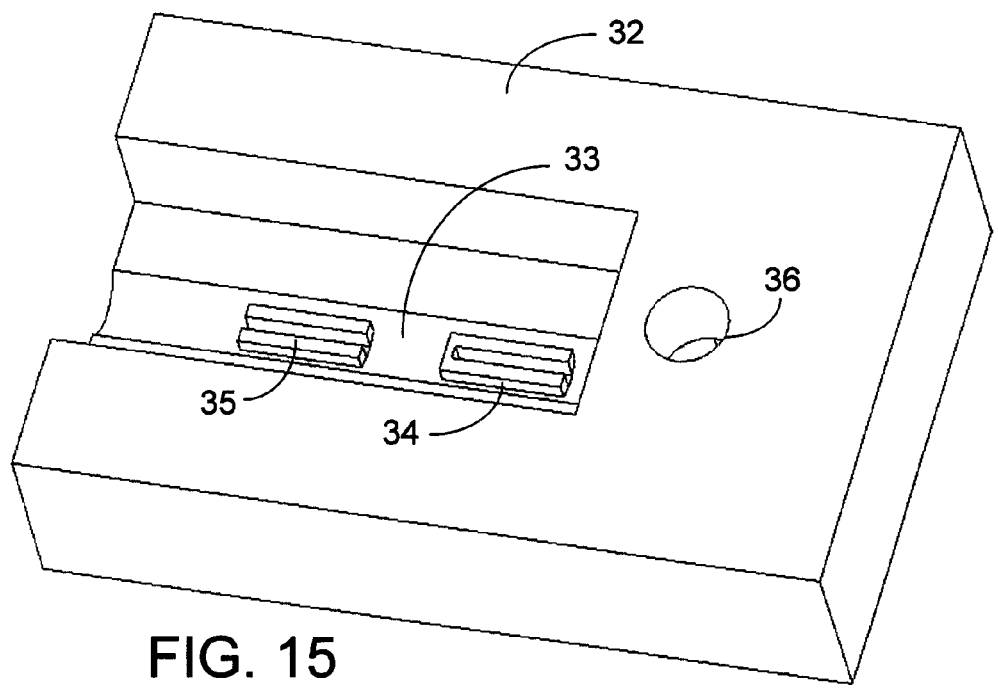
FIG. 15 is an isometric sectional view of a capillary channel residing on a "chip" that contains one or more internal elements that functions to meter the source liquid via its geometry and surface finishes. Once on the chip, samples are manipulated through the channels of the chip to perform the steps required for mixing, incubation, reaction, separation, and detection. Movement through the channels is controlled using a combination of pressure and/or voltage, as known in the art.
Figure 15A:
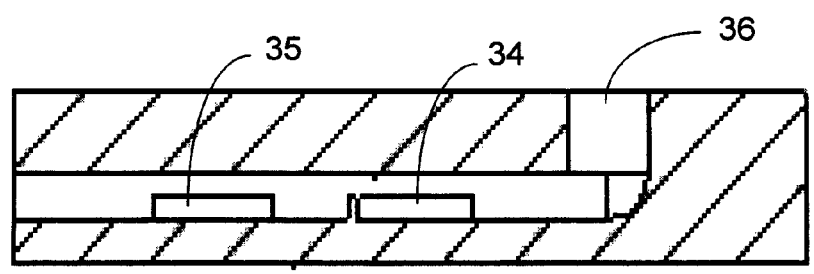
FIG. 15A is a cross-sectional side view of the capillary chip illustrated in FIG. 15.

Referring to FIGS. 15-15A, a chip 32 is shown to include multiple pockets. Chip 32 is a laminated plate that defines multiple capillary channels to move liquid. Once on the chip, a source liquid sample is manipulated through the channels of the chip to perform the steps required for mixing, incubation, reaction, separation, and detection. Movement through the channels is controlled using a combination of pressure and/or voltage. For a clear visual in the drawing, the chip 32 is cut along its centerline to expose the internal pocket 34 and 35. The capillary channel 33 is connected to an input orifice 36. A pipetting device (not shown) containing the source liquid (not shown) connects to the input orifice 36. The pipetting device moves the source liquid past the internal pocket 34 and 35, and then retracts the liquid back out of the input orifice 36. The internal pockets 34 and 35 now contain a precise amount of source liquid (not shown). The pipetting device reattaches to the chip 32 input orifice 36 and deposits a slug of diluent (not shown). The pipetting device moves the diluent back and forth past the pockets 34 and 35 thereby mixing the source liquid and the diluent. When the pipetting device disconnects from the input orifice 36, a precise mixture is left in the capillary channel 33.

Figure 16:
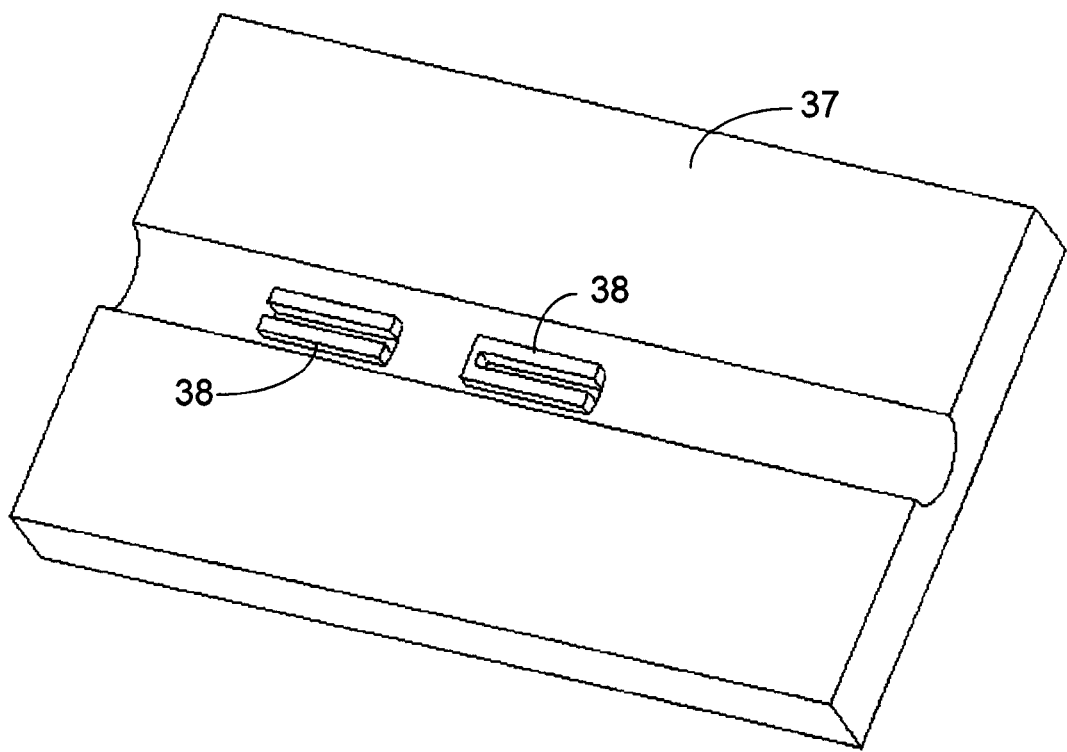
FIG. 16 is a sectional view of a plate that contains one or more internal elements that function to meter the source liquid via their geometry and surface finish.

In FIG. 16, a plate 37 is shown that contains multiple pockets 38. A device containing source liquid can drag the source liquid past the pockets 38 and deposit a fixed amount of source liquid.

Figure 17:
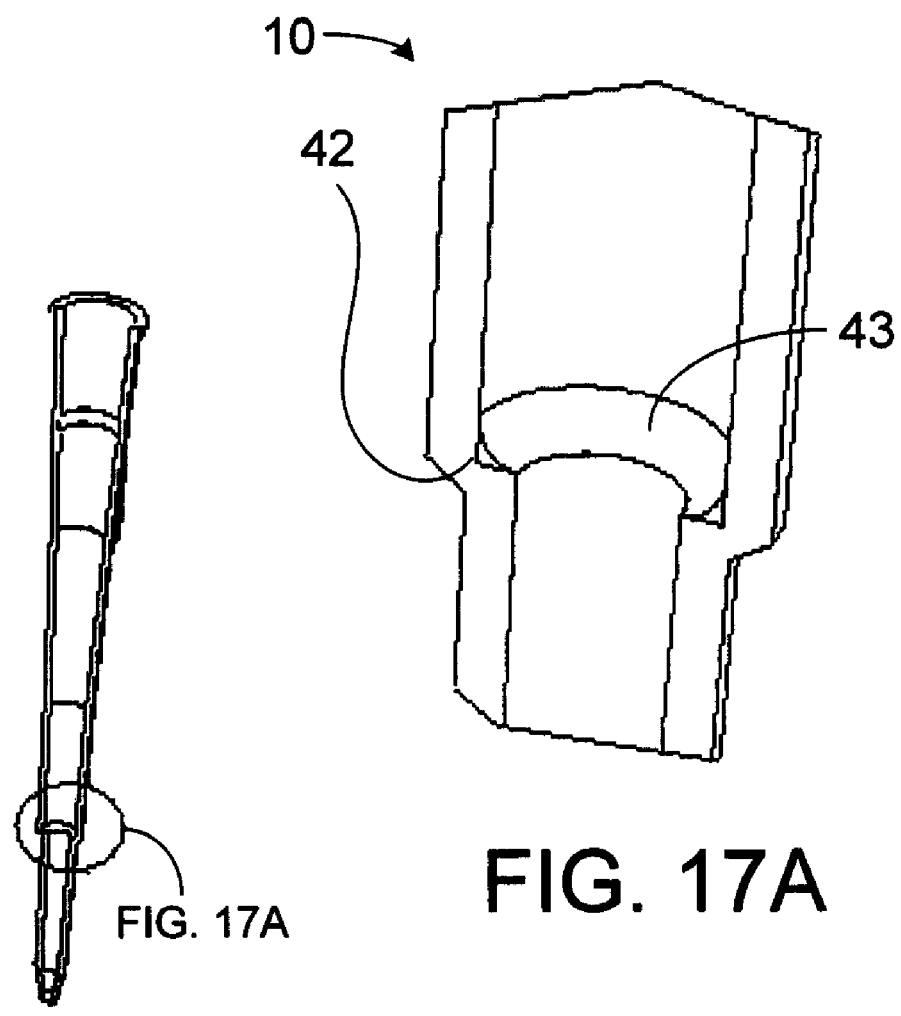
FIG. 17 is a cross-sectional view of a pipette tip that includes a radial ledge that forms a capillary retention feature.
Figures 18, 18A:
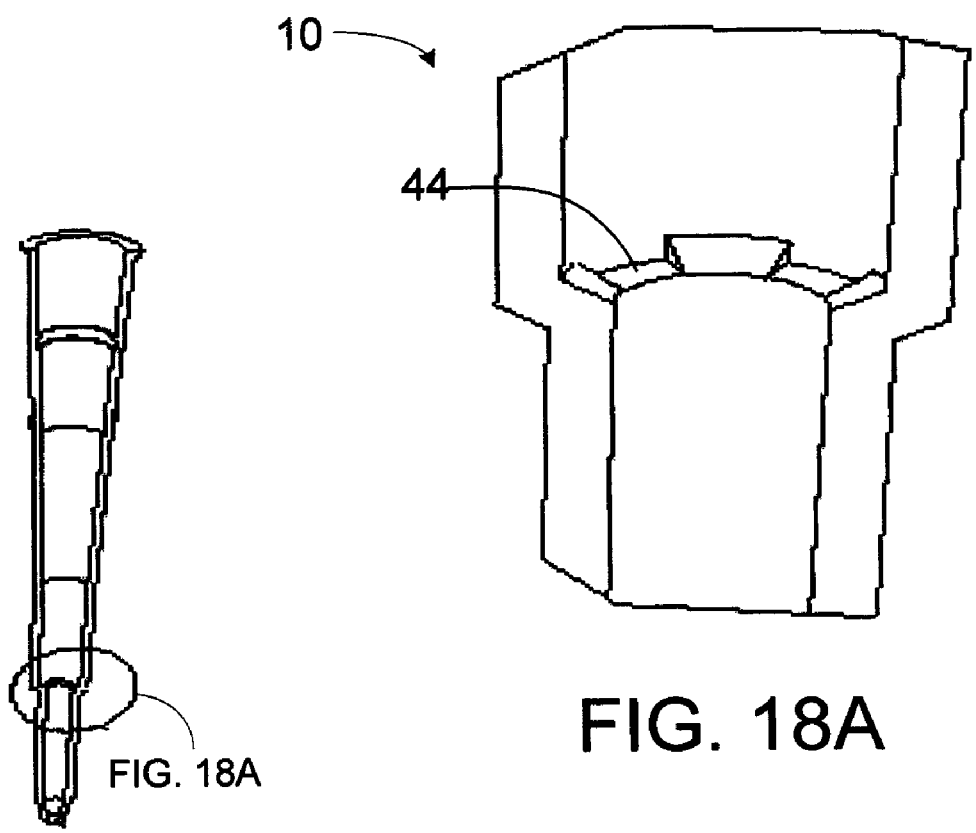
FIG. 18 is a cross-sectional view of a pipette tip that includes a series of radial ledges that form capillary retention features and FIG. 18A is an enlarged view of area 18A in FIG. 18.

Referring to FIGS. 17-17A, pipette tip 10a includes a continuous radial ledge 42 that acts as a capillary retention feature. A predetermined, metered dose of the sample liquid 43 is captured and retained by capillary force on the ledge. In the pipette tip 10b of FIGS. 18 and 18A, the metered dose of the sample liquid is captured and retained by capillary force in a series of discrete ledge sections 44.

Devices according to the invention can be designed for compatibility with various liquids, including aqueous buffers, organic solvents, e.g., dimethylsulfoxide (DMSO), acids, bases, proteins, oligonucleitides and reagents. Compatibility is achieved by selection of suitable materials for fabrication of components that contact the liquid.

Exemplary materials for fabrication of components are stainless steel, nylon, polyethylene, polypropylene, EPD rubber, silicone rubber and polytetrafluoroethylene (PTFE; Teflon®). Suitable materials and fabrication of components is within ordinary skill in the art.

A number of embodiments of the invention have been described. Nevertheless, it will be understood that various modifications may be made without departing from the spirit and scope of the invention. For example, the internal pocket could be no more than a surface texture or chemical or biological adherent, enabling a small amount of source liquid to adhere where the texture or adherent is present, including any small feature, additional part or surface enhancement such as finish roughness, chemistry or biology, (internal or external) that can trap and retain liquid due to capillary force, surface energy, gravity, chemistry bonding or biological bonding (or a combination of all). Accordingly, other embodiments are within the scope of the following claims.

What is claimed is:

1. A method of mixing a sample liquid with a diluent liquid, the method comprising:
   providing a device tip including:
   an elongated body having an outer surface and an interior wall, a portion of the interior wall defining an internal cavity open at a lower end of the body; the body defining an opening in an upper portion of the body, through which air can be drawn from the cavity to draw liquids into the cavity through the lower end of the body; wherein the portion of the interior wall defining the internal cavity also defines a pocket open to the internal cavity, the pocket radially extending into the portion of interior wall defining the internal cavity, the pocket sized and configured to collect a dose of a liquid drawn into the cavity and to retain the dose of the liquid as the cavity is otherwise evacuated;
   drawing a sample liquid into the device tip;
   collecting a dose of the sample liquid in the pocket of the device tip;
   retaining the dose of the sample liquid in the pocket of the device tip while expelling the sample liquid from the internal cavity of the device tip; and then
   drawing a volume of a diluent liquid into the device tip a sufficient distance to contact the retained dose of sample liquid to induce mixing of the diluent liquid with the dose of sample liquid.

2. The method according to claim 1 further comprising, after expelling the sample liquid from the device tip and before drawing the volume of diluent liquid into the device tip, drawing a cleaning liquid into the device tip below the pocket; and then expelling the cleaning liquid from the device tip to flush any residual sample liquid from surfaces of the interior wall below the pocket.

3. The method according to claim 1 further comprising dispensing a metered volume of the mixture into a destination well.

4. The method according to claim 3 wherein dispensing the metered volume comprises pneumatically propelling the mixture from the device tip.

5. The method according to claim 3 wherein the device tip further defines a capillary hole between an outer surface of the device tip and the internal cavity.

6. The method according to claim 5 wherein the mixture is propelled from the device tip by forcing a pressurized gas into the internal cavity through the capillary hole.

7. The method according to claim 1 wherein the internal cavity is narrower at a lower open end of the device tip than in an upper section of the device tip.

8. The method according to claim 7 wherein the pocket is disposed in a portion of the internal cavity wider than the internal cavity at the open end of the device tip.

9. The method according to claim 1 wherein the device tip defines a plurality of said pockets spaced apart from one another.

10. The method according to claim 1 wherein the diluent liquid is moved reciprocally across the pocket multiple times, to induce mixing with the dose of sample liquid.

11. A method of metering and mixing a plurality of doses of a sample liquid with a diluent liquid, the method comprising;
    providing an array of device tips, each device tip comprising an elongated body having an outer surface and an interior wall, a portion of the interior wall defining an internal cavity open at a lower end of the body; the body defining an opening in an upper portion of the body, through which air can be drawn from the internal cavity to draw liquids into the cavity through the lower end of the body; wherein the portion of the interior wall defining the internal cavity also defines a pocket open to the internal cavity, the pocket extending into the portion of interior wall defining the internal cavity, the pocket sized and configured to collect a dose of a sample liquid;
    collecting a dose of the sample liquid in the pocket of each device tip;
    retaining the dose of the sample liquid in the pocket of each device tip while expelling the sample liquid from the internal cavity of the device tip; and then
    drawing a diluent liquid into the device tips a sufficient distance to contact the retained doses of sample liquid, to induce mixing of the diluent liquid with the doses of sample liquid.

12. The method according to claim 11 further comprising, after expelling the sample liquid from the device tips and before drawing the diluent liquid into the device tips, drawing a cleaning liquid into the device tips below the pockets; and then expelling the cleaning liquid from the device tips to flush any residual sample liquid from surfaces of the interior wall below the pocket.

13. The method according to claim 11 further comprising dispensing from each device tip a metered volume of the mixture into a destination well.

14. The method according to claim 13 wherein dispensing the metered volume comprises pneumatically propelling the mixture from the device tips.

15. The method according to claim 14 wherein the mixture is propelled from the device tips by forcing a pressurized gas into the internal cavities of the device tips through capillary holes between outer surfaces of the device tips and the internal cavities of the device tips.

16. The method according to claim 11 wherein the internal cavity is narrower at a lower open end of the device tip than in an upper section of the device tip.

17. The method according to claim 16 wherein the pocket is disposed in a portion of the internal cavity wider than the internal cavity at the open end of the device tip.

18. The method according to claim 16 further comprising dispensing a metered volume of the mixture into an array of liquid-receiving units.

19. The method according to claim 18 wherein the array of liquid-receiving units is a multi-well container.

* * * * *